United States Patent
Windheuser

(10) Patent No.: US 7,186,224 B2
(45) Date of Patent: Mar. 6, 2007

(54) SIDE ATTACHING GUIDEWIRE TORQUE DEVICE

(75) Inventor: James E. Windheuser, Hopkinton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/426,134

(22) Filed: Apr. 28, 2003

(65) Prior Publication Data

US 2004/0215108 A1  Oct. 28, 2004

(51) Int. Cl.
*A61B 5/00* (2006.01)
*A61M 25/00* (2006.01)

(52) U.S. Cl. ...................................................... 600/585

(58) Field of Classification Search ........ 600/433–435, 600/585; 16/110.1, 422, 434; 24/129 R, 24/570; 248/353; 81/119, 487–489; 140/2, 140/149; 606/1, 108; 604/164.13, 165.01, 604/165.02, 166.04, 177, 178, 103.04, 523, 604/528, 533, 539

See application file for complete search history.

(56) References Cited

U.S. PATENT DOCUMENTS

| 160,315 | A | * | 3/1875 | Fuller ......................... 248/353 |
|---|---|---|---|---|
| 2,742,253 | A | * | 4/1956 | July ............................ 248/353 |
| 3,248,089 | A | * | 4/1966 | Barney ........................ 258/48 |
| 4,598,708 | A | | 7/1986 | Beranek |
| 4,726,369 | A | * | 2/1988 | Mar .............................. 606/1 |
| 4,858,810 | A | | 8/1989 | Intlekofer et al. |
| 5,137,517 | A | | 8/1992 | Loney et al. |
| 5,161,534 | A | * | 11/1992 | Berthiaume ................. 600/434 |
| 5,312,338 | A | | 5/1994 | Nelson et al. |
| 5,392,778 | A | | 2/1995 | Horzewski |
| 5,423,331 | A | * | 6/1995 | Wysham ..................... 600/585 |
| 5,660,133 | A | * | 8/1997 | Munich ....................... 114/219 |
| 5,851,189 | A | | 12/1998 | Forber |
| 6,030,349 | A | * | 2/2000 | Wilson et al. .............. 600/585 |
| 6,485,466 | B2 | | 11/2002 | Hamilton |
| 6,517,518 | B2 | * | 2/2003 | Nash et al. ............ 604/164.02 |

FOREIGN PATENT DOCUMENTS

| DE | 20107 131 U1 | 9/2001 |
|---|---|---|
| EP | 1 346 746 A1 | 9/2003 |

* cited by examiner

*Primary Examiner*—Max F. Hindenburg
*Assistant Examiner*—Brian Szmal
(74) *Attorney, Agent, or Firm*—Christensen O'Connor Johnson Kindness PLLC

(57) ABSTRACT

A guidewire torque device formed from a single piece that may be either molded or machined. The device includes an insertion slot for receiving a guidewire, such that the device does not have to be backloaded over the end of the guidewire. Two rotation slots, provided in opposite sides of the device, allow the device to be rotated so as to secure the guidewire within the device. The rotation slots terminate at a hole in the center of the device that is sized to secure a guidewire of a selected diameter. The device can be operated by a physician with a single hand, and is particularly useful during rapid exchange procedures.

2 Claims, 4 Drawing Sheets

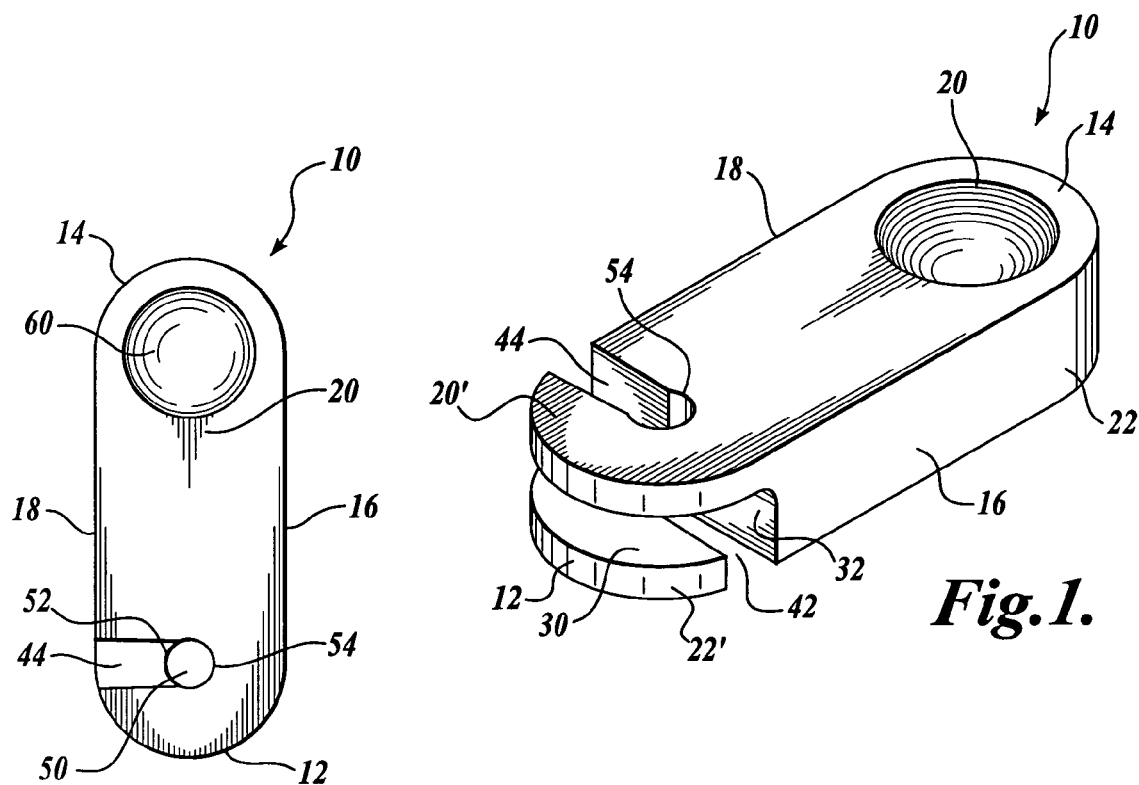
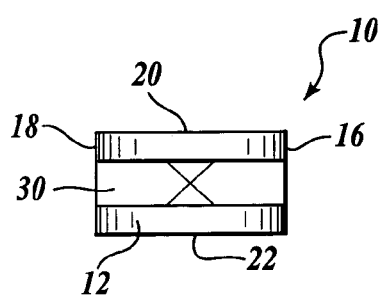
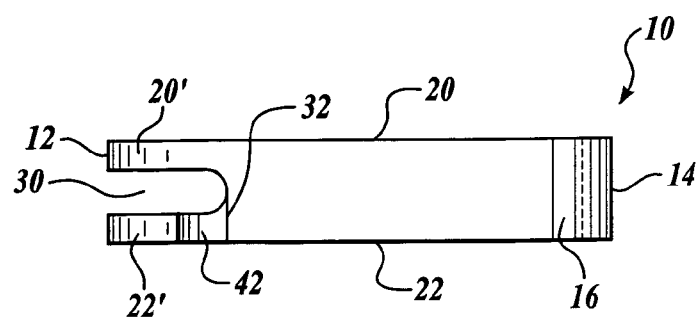

SIDE ATTACHING GUIDEWIRE TORQUE DEVICE

FIELD OF THE INVENTION

The present invention relates to a guidewire torque device for use in catheter procedures within the human anatomy. More particularly, the present invention relates to a guidewire torque device that can be attached from the side of the guidewire and that can be operated with one hand.

BACKGROUND OF THE INVENTION

Guidewires are used in most catheter-based procedures. The distal end of a guidewire typically has an angled tip, which can be oriented to help steer the guidewire through curves and junctions of the vasculature or vessels of a patient. The orientation of the angled tip is achieved by torqueing the guidewire so that it rotates about its axis. However, since the guidewire has a small diameter and typically a smooth surface, it is difficult to torque with an operator's fingers. Torqueing requires the aid of a larger diameter torque device, which is attached to the guidewire.

One common type of prior art torque device is referred to as a pin-vise device. A pin-vice device has a structure somewhat similar to a miniature drill chuck with a cylindrical handle. The device has multiple parts. A cap is screwed down over a collet, which in turn grips a guidewire running through the collet. The device is typically backloaded over the guidewire from the proximal end. The cap is rotated with respect to the handle, which tightens the collet and grips the wire. At that point, the device can aid in the manipulation of the guidewire, either rotational or longitudinal. Among the disadvantages of the pin-vise-type torque device is that it has multiple parts and requires two hands to operate. In addition, the device must be backloaded over the proximal end of guidewire.

An example of a prior art pin-vice type torque device is shown in U.S. Pat. No. 5,851,189, to Forber. The '189 patent teaches a torque device for attaching to and selectively gripping and releasing a catheter guidewire to permit rotational and longitudinal manipulation of the guidewire to steer the guidewire through a vessel. A spindle is threadably engaged in a cap, and a bore through the spindle aligns with a bore through the cap to accept the guidewire. The end of the spindle inside the cap has a pair of fingers straddling the guidewire. As the cap and spindle are rotated with respect to each other, the threaded engagement of the spindle and cap forces the end of the fingers to advance along a tapering bore in the cap, which causes the fingers to close and grip the guidewire. Reversing the direction of rotation releases the grip on the guidewire.

Another prior art guidewire torque device is shown in U.S. Pat. No. 5,392,778, to Horzewski. The '778 patent teaches a torque device that is backloaded over the end of a guidewire and which a user can then operate with a single hand to grip the guidewire and to release the guidewire. The device is formed from a pair of tubular members, one of which terminates at one end in a multitude of prongs and the other fitting over the prongs in a manner permitting it to slide relative to the prongs and to the first tubular member in the axial direction. The tubular members are hollow to permit passage of the guidewire, and the tips of the prongs encircle the central axis of the device, likewise to permit passage of the guidewire. The prongs are shaped such that their tips are far enough apart to permit unimpeded axial movement of the device over the guidewire, but the prongs are of a resilient construction, permitting them to be bent or compressed toward each other to grip the guidewire on all sides. A circular protrusion or ring on the interior of the second tubular member extending inward contacts the sloping outer surfaces of the prongs such that when the second tubular member is slid over the prongs with the ring moving toward the prong tips, the ring compresses the prongs, causing the tips to close over and grip the guidewire. The two tubular members are readily moved relative to each other with a single hand. Thus, once the device is backloaded over the end of the guidewire, a single hand may be used to make the device both grip the guidewire and release the guidewire.

Another prior art guidewire torque device is shown in U.S. Pat. No. 5,312,338. The '338 patent teaches a guidewire torque device formed as a gripping-knob rotational tool. The device includes a slot for engaging the guidewire from the side. The device is comprised of a tubular housing that is formed from two cylindrical members that are adapted to fit together in a telescoping arrangement. The two members are provided with a passageway that runs through the length of each member. A slot also runs the length of each member and extends from an outer surface of each member to the passage way running therethrough. In operation, the guidewire is placed into the longitudinal slot and the two cylindrical members can then be rotated relative to each other to a first position which locks the guidewire within the device, but without securing the guidewire to the device. In this position, the device is in a first gripping mode. The cylindrical members can then be rotated to a second position which causes an elastomeric member to twist around the guidewire, but without bending the guidewire.

One of the disadvantages of prior art guidewire torque devices such as those shown above is that they require multiple moving parts which are subject to breakage, and which are relatively costly to manufacture. In addition, devices such as those taught in the '189 and '778 patents must generally be backloaded over the proximal end of the guidewires. Furthermore, the devices of the '338 and '189 patents generally require two hands to operate.

SUMMARY OF THE INVENTION

The present invention is directed to providing a guidewire torque device that may be formed from a single component and which can be attached from the side of a guidewire using only one hand. Such guidewire torque device can be easily attached to a guidewire.

In accordance with one aspect of the invention, the guidewire torque device is formed from a single piece of material that can be molded or machined, for example. The single piece design allows the device to be easily operated with only one hand, and is simpler and less costly to manufacture than multiple-part prior art devices.

In accordance with another aspect of the invention, the device can be attached from the side of a guidewire. The use of a side-loading method can help avoid damage to guidewires that have delicate proximal ends that might otherwise be harmed by the backloading process of a conventional torque device. In addition, the side-loading technique contributes to the simplicity that makes the device easy to operate using only a single hand.

In accordance with another aspect of the invention, the device includes an insertion slot and one or more rotation slots. In a preferred embodiment, the insertion slot is located at the end of the device, such that the insertion slot can be used to engage the guidewire from the side. Two rotation slots are also provided, such that once the guidewire is inside the insertion slot, the device may be rotated. The rotation slots allow the device to rotate with respect to the guidewire such that the guidewire becomes secured in a hole in the center of the device. This configuration further contributes to the simplicity of the operation of the device which allows the device to be used with one hand. Furthermore, the simplicity of the operation of the device allows the device to be quickly unlocked and moved to other desired locations on the guidewire, which makes the device particularly useful during rapid exchange procedures.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a top front perspective of a guidewire torque device in accordance with the present invention;

FIG. 2A is a top plan thereof, without hidden lines;

FIG. 2B is a front end elevation thereof, without hidden lines;

FIG. 2C is a side elevation thereof, without hidden lines;

DETAILED DESCRIPTION OF THE PREFERRED EMBODIMENT

Figure 3A:
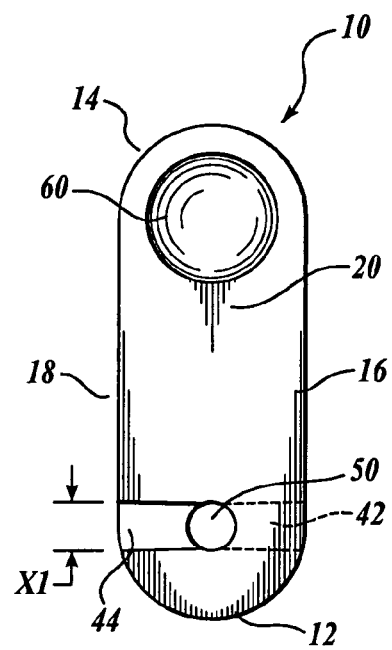
FIG. 3A is a top plan thereof, with hidden lines.

The guidewire torque device 10 in accordance with the present invention, shown in FIG. 1 is formed of a single piece of material, which may be molded or machined. The guidewire torque device 10 includes a front or distal end 12, a back or proximate end 14, opposite sides 16, 18, a top surface 20, and a bottom surface 22. An insertion slot 30 of constant width extends from the front end 12 toward the back end of the device, the full width of the device (i.e., from and through the opposite sides 16, 18), and terminates at a plannar base 32 extending perpendicular to both the sides 16, 18 and top and bottom surfaces 20, 22. The insertion slot divides the front or distal end portion of the device into thin and flat top and bottom bifurcations 20', 22', respectively. The facing surfaces of the bifurcations are plannar, orthogonal to the base 32, and spaced apart a uniform distance which, as described below, is slightly greater than the predetermined diameter of a guidewire of the type with which the device is to be used. A first rotation slot 42 extends inward from one side 16 at the base of the bottom bifurcation or finger 22', while a second rotation slot 44 extends inward from the side 18 at the base of the top bifurcation or finger 20'. The inner end portion 52 of rotation slot 42 is essentially semicircular, and the inner end portion of rotation slot 44 is essentially semicircular (as seen at 54 in FIG. 1, for example). The semicircular end portions of the two rotation slots overlap at the transverse center of the device, forming a straight through hole 50 which is unobstructed from the top surface 20 to the bottom surface 22 and which extends orthogonally between such surfaces. Stated in another way, the length of the circular hole 50 is parallel to the flat sides 16, 18, and midway therebetween, at the base 32 of the insertion slot 30 and at the inner end portions of the rotation slots 42, 44.

The guidewire torque device 10 allows a physician to attach the device from the side of a guidewire with one hand. Furthermore, the physician is also able to quickly unlock and move the guidewire torque device 10 to other locations on the guidewire. These features are particularly useful during rapid exchange procedures. The guidewire torque device 10 is also useful for guidewires that have delicate proximal ends where damage could occur if a prior art torque device were backloaded over the end.

The forming of the guidewire torque device 10 from a single part, which can be molded or machined, reduces the complexity and expense of the device. As will be described in more detail below, in one embodiment the design of the rotation slots 42 and 44 and their semicircular inner end portions 52 and 54 are particularly important aspects. The slots 42 and 44 and end portions 52 and 54 may be designed to be size specific for selected guidewires. In addition, the overall shape of the guidewire torque device 10 can be modified to be more ergonomic, if desired. Furthermore, a protrusion or spindle extending 90° from the device, may assist the operator in rotating the torque device 10 similar to how a conventional prior art pin-vice-type torque device is operated. Other external structures such as knurls, ridges, or a textured pattern, may also be used to assist in rotating the guidewire torque device 10.

FIG. 2A is a top view without hidden lines of the guidewire torque device 10 of FIG. 1. The front end 12, back end 14, side 16, side 18, and top surface 20 of the guidewire torque device 10 are referenced. A grip depression 60 is also shown located in the top surface 20. From the top view of FIG. 2A, the rotation slot 44 and its end portion 54 are also visible, along with the end portion 52 of the other insertion slot.

FIG. 2B is an end view without hidden lines of the guidewire torque device 10. The side 16, side 18, top surface 20, and bottom surface 22 of the guidewire torque device 10 are referenced. From the end view of FIG. 2B, the insertion slot 30 extending form the front end 12 is visible.

FIG. 2C is a side view without hidden lines of the guidewire torque device 10. The front end 12, back end 14, side 16, top surface 20, and bottom surface 22 of the guidewire torque device 10 are referenced, along with the bifurcations or fingers 20', 22'. From the side view of FIG. 2C, the insertion slot 30, the base 32 of the insertion slot, and the rotation slot 42 are also visible.

FIG. 3A is a top view with hidden lines of the guidewire torque device 10. The hidden lines of FIG. 3A further illustrate the rotation slot 42 that extends inward from the side 16. A dimension X1 of the hole 50 is also illustrated, such hole being formed by the semicircular end portions 52, 54. An example value for the dimension X1 will be described in more detail below. In various embodiments, the rotation slots 42 and 44 may generally have slightly tapered or straight configurations.

Figure 3B:
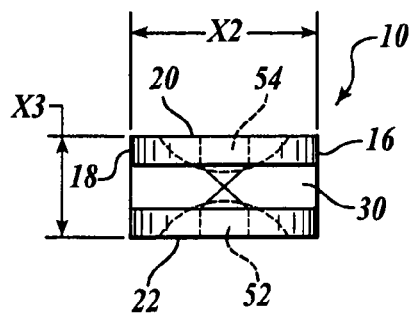
FIG. 3B is a front end elevation thereof, with hidden lines.

FIG. 3B is an end view with hidden lines of the guidewire torque device 10. Note dimension X2 for the width and a dimension X3 for the height of the guidewire torque device 10. Example values for the dimensions X2 and X3 will be described in more detail below.

Figure 3C:
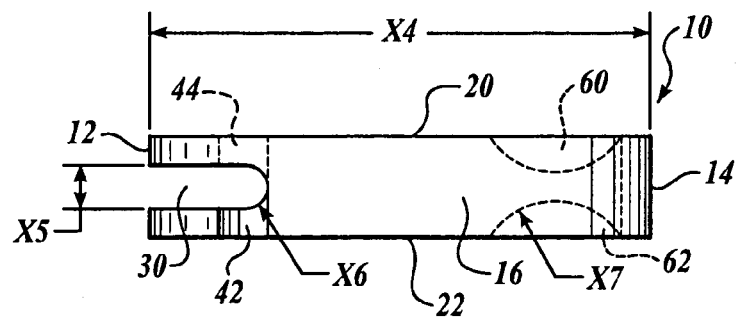
FIG. 3C is a side elevation thereof, with hidden lines.

FIG. 3C is a side view with hidden lines of the guidewire torque device 10. The hidden lines of FIG. 3C further illustrate a grip depression 60 and a grip depression 62. The hidden lines also illustrate the rotation slot 44. Also shown in FIG. 3C are a dimension X4 for the length of the guidewire torque device, a dimension X5 for the width of the insertion slot 30 (between the bifurcations), a dimension X6 for the opening width of the rotation slots 42 and 44, and a dimension X7 for the radius of the grips 60 and 62.

The dimensions of the guidewire torque device may be designed to be size specific for particular guidewires. As an example, in one embodiment the dimension X4 which represents the length of the guidewire torque device may be designated as 1.000 units. The dimension X1 representing the diameter of the hole 50 may be designated as 0.093 units. The dimension X2 representing the width may be designated as 0.374 units. The dimension X3 representing the overall height may be designated as 0.200 units. The dimension X5 representing the width of the insertion slot 30 may be designated as 0.093 units (the same as the diameter of composite hole 50). The dimension X6 representing the opening width of the rotation slots 42 and 44 may be designated as 0.098 units (slightly greater than that diameter of the hole 50, i.e., a very slight taper in the width of each rotation slot). The dimension X7 representing the radius of the grips 60 and 62 may be designated as 0.156 units.

Figure 4A:
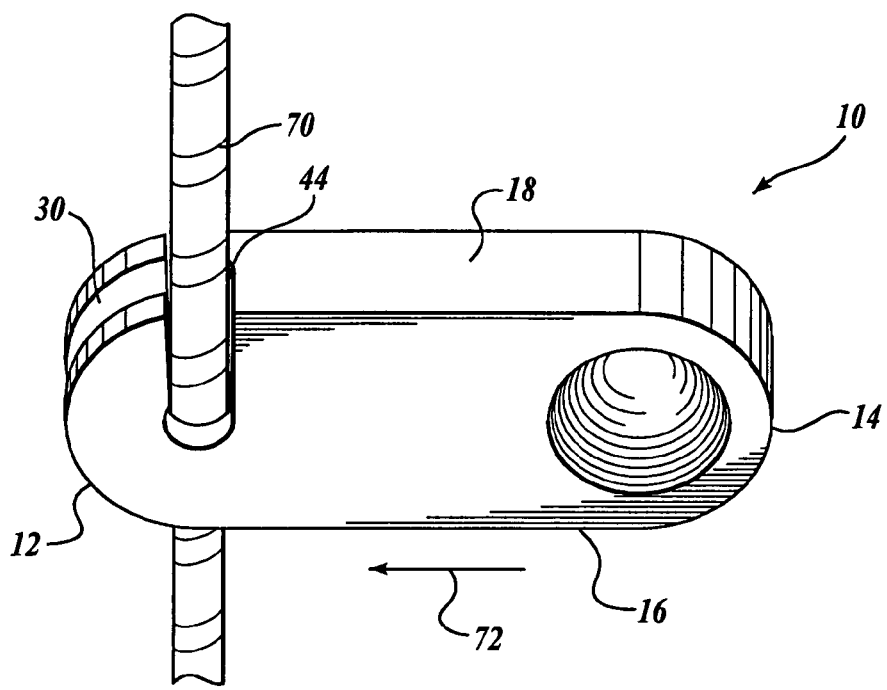
FIG. 4A is a three-dimensional view of the guidewire torque device of FIG. 1 illustrating a guidewire being slid into the insertion slot.
Figure 4B:
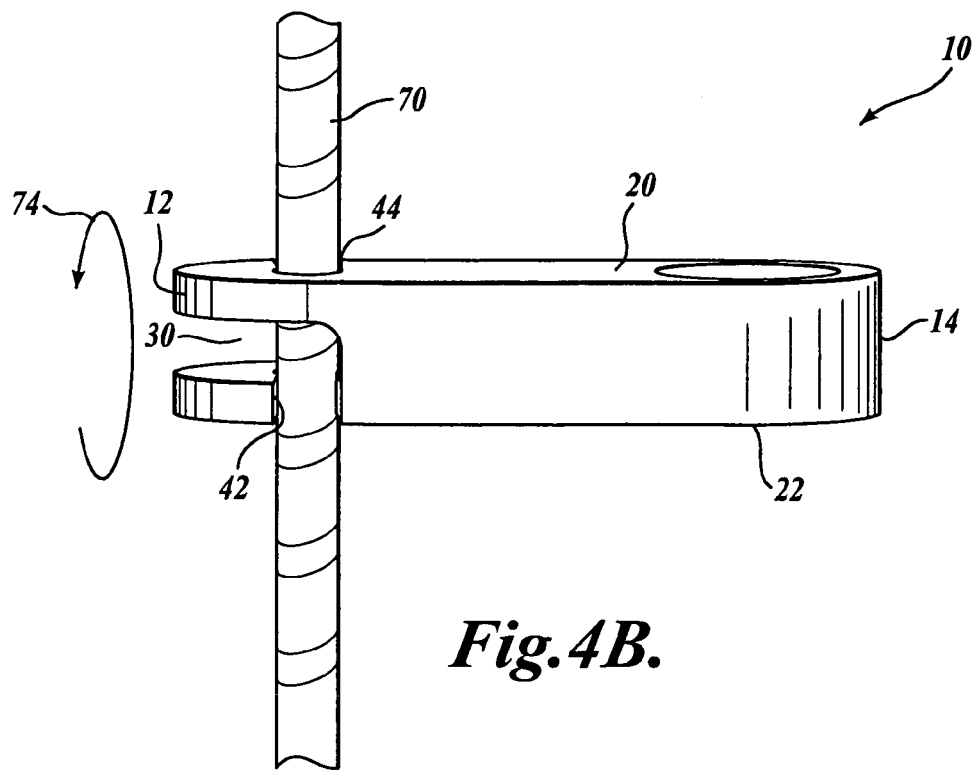
FIG. 4B is a three-dimensional view of the guidewire torque device of FIG. 4A after rotating the rotation slots around the guidewire so as to lock the guidewire into the device.

FIGS. 4A and 4B illustrate the operation of inserting and locking a guidewire into the guidewire torque device 10. As shown in FIG. 4A, the guidewire torque device 10 is moved in a direction indicated by arrow 72 toward a guidewire 70, such that the guidewire 70 is caused to enter the insertion slot 30. The guidewire 70 rests against the flat base 32 of the guidewire torque device 10. The guidewire 70 is partially visible through the rotation slot 44. The diameter of the guidewire is slightly less than the width of the insertion slot and the width of each rotation slot, as well as the composite center hole.

In the position of FIG. 4B, the guidewire torque device 10 has been rotated in a direction indicated by arrow 74. The rotation of the guidewire torque device 10 locks the guidewire 70 into the device. More specifically, the guidewire 70 has been rotated through the rotation slots 42 and 44 so as to gently pinch lock the guidewire 70 between the semicircular portions 52 and 54, a position just past 90° rotation from the insertion portion.

It will be appreciated that the guidewire torque device 10 as described above can easily be attached to a guidewire. A physician is able to attach the guidewire torque device 10 from the side of the guidewire, thus not requiring the device to be backloaded over the end of the guidewire as was required in certain prior art torque devices. Furthermore, the guidewire torque device 10 can be operated by a physician with a single hand. These features of the guidewire torque device 10 are particularly useful during rapid exchange procedures.

Figure 5:
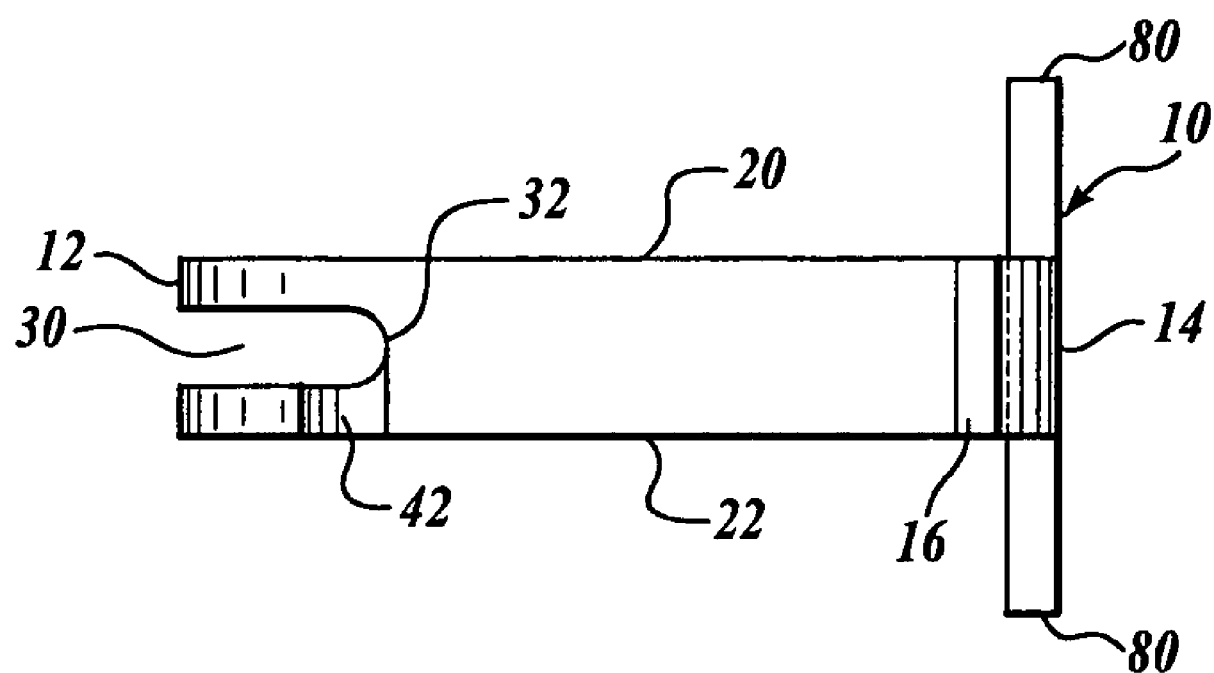
FIG. 5 is a side view of a guidewire torque device with a protrusion for assisting with the rotation of the device.

While the preferred embodiment of the invention has been illustrated and described, it will be appreciated that various changes can be made therein without departing from the spirit and scope of the invention. For example, as illustrated in FIG. 5, a protrusion 80 could be extended from the guidewire torque device at a 90 degree angle in order to assist with the rotation of the device. In addition, a smaller or larger guidewire slot or hole could be made on the guidewire torque device to accommodate different guidewire diameters. The interior of the rotation slots could be roughened or shaped like a knife to better grip the guidewire. The length of the hole could be made longer so as to increase friction for holding the guidewire. The handle portion of the guidewire torque device could be divided in any number of forms, each of which could be generally directed to making the gripping of the guidewire torque device more ergonomic for the user. A second set of insertion and rotation slots could be provided at the other end of the guidewire torque device to accommodate a different guidewire diameter. A high friction (i.e., rubber, sandpaper, etc.) coating could be added to the interior of the rotation slot so as to allow for better gripping of the guidewire during a procedure. In general, the torque device of the present invention may be utilized with any medical instrument that is similar to a guidewire. In addition to endoscopy guidewires, the guidewire torque device can be used with any catheter-based guidewires (cardiology, peripheral vascular, neurology, urology, pulmonary, etc.).

The embodiments of the invention in which an exclusive property or privilege is claimed are defined as follows:

1. A torque device, the device having a length, width and height and being useable to apply torque to a guidewire of a predetermined diameter, the device comprising:

a single piece of material having a distal end, a proximate end, opposite sides, a top surface and a bottom surface, said piece having an insertion slot of constant width extending from the distal end toward the proximate end and from one of the opposite sides to the other of the opposite sides, the constant width of the insertion slot being greater than the predetermined diameter of the guidewire for receiving the guidewire such that the device does not have to be back loaded over the end of the guidewire, the insertion slot dividing the distal end portion of the piece into thin and flat top and bottom bifurcations, respectively, such bifurcations having parallel planar facing surfaces, the insertion slot terminating at a flat base disposed orthogonal to the planar facing surfaces of the bifurcations, a first rotation slot extending inward from one side of the piece at the base of the bottom bifurcation, and a second rotation slot extending inward from the opposite side of the piece at the base of the top bifurcation, the rotation slots having respective inner end portions essentially semicircular and overlapping to form a straight through hole from the top surface to the bottom surface, such hole being unobstructed and extending orthogonally between such surfaces such that the axis of the hole is parallel to the opposite sides and located midway therebetween at the base of the insertion slot, each rotation slot extending perpendicularly inward from a side of the piece and being of a width greater than the predetermined diameter of the guide wire, whereby, with the guidewire inserted into the insertion slot to the base thereof, the piece is rotatable for reception of the guidewire along the insertion slots until the guidewire is pinched in the central hole for applying torque to the guidewire by movement of the piece.

2. A method for securing a medical instrument guidewire of a predetermined diameter to a torque device, such torque device having a length, width and height and being useable to apply torque to a guidewire of a predetermined diameter, the device comprising:

a single piece of material having a distal end, a proximate end, opposite sides, a top surface and a bottom surface, said piece having an insertion slot of constant width extending from the distal end toward the proximate end and from one of the opposite sides to the other of the opposite sides, the constant width of the insertion slot being greater than the predetermined diameter of the guidewire for receiving the guidewire such that the device does not have to be back loaded over the end of the guidewire, the insertion slot dividing the distal end portion of the piece into thin and flat top and bottom bifurcations, respectively, such bifurcations having parallel planar facing surfaces, the insertion slot terminating at a flat base disposed orthogonal to the planar facing surfaces of the bifurcations, a first rotation slot extending inward from one side of the piece at the base of the bottom bifurcation, and a second rotation slot extending inward from the opposite side of the piece at the base of the top bifurcation, the rotation slots having respective inner end portions essentially semicircular and overlapping to form a straight through from the top surface to the bottom surface, such hole being unobstructed and extending orthogonally between such surfaces such that the axis of the hole is parallel to the opposite sides and located midway therebetween at the base of the insertion slot, each rotation slot extending perpendicularly inward from a side of the piece and being of a width greater than the predetermined diameter of the guide wire;

which method comprises:

fitting the insertion slot transversely over the guidewire from a side of the guidewire until the guidewire is received in the base of the insertion slot;

rotating the piece for reception of the guidewire along the insertion slots until the guidewire is pinched in the central hole; and moving the piece to apply torque to the guidewire.

* * * * *

UNITED STATES PATENT AND TRADEMARK OFFICE
CERTIFICATE OF CORRECTION

PATENT NO.       : 7,186,224 B2
APPLICATION NO.  : 10/426134
DATED            : March 6, 2007
INVENTOR(S)      : J.E. Windheuser It is certified that error appears in the above-identified patent and that said Letters Patent is hereby corrected as shown below:

| COLUMN | LINE | |
|--------|------|---|
| 7 | 12 | "through from" should read --through hole from-- |

Signed and Sealed this

Thirty-first Day of July, 2007

JON W. DUDAS
*Director of the United States Patent and Trademark Office*